(12) United States Patent
Priewe

(10) Patent No.: US 11,229,510 B2
(45) Date of Patent: *Jan. 25, 2022

(54) SURGICAL IMPLANT AND PROCESS OF MANUFACTURING THEREOF

(71) Applicant: Cilag GMBH International, Zug (CH)

(72) Inventor: Jorg Priewe, Kiel (DE)

(73) Assignee: Cilag GMBH International, Zug (CH)

( * ) Notice: Subject to any disclaimer, the term of this patent is extended or adjusted under 35 U.S.C. 154(b) by 153 days.

This patent is subject to a terminal disclaimer.

(21) Appl. No.: 16/712,512

(22) Filed: Dec. 12, 2019

(65) Prior Publication Data

US 2020/0113665 A1     Apr. 16, 2020

Related U.S. Application Data

(63) Continuation of application No. 15/259,227, filed on Sep. 8, 2016, now Pat. No. 10,588,731.

(30) Foreign Application Priority Data

Oct. 30, 2015   (DE) .......................... 102015013992.4

(51) Int. Cl.
*A61F 2/00*   (2006.01)
*A61L 27/34*   (2006.01)
(Continued)

(52) U.S. Cl.
CPC ............ *A61F 2/0063* (2013.01); *A61L 27/34* (2013.01); *A61L 27/50* (2013.01); *A61L 27/56* (2013.01);
(Continued)

(58) Field of Classification Search
CPC .................. A61F 2/0063; A61F 2/0077; A61F 2002/0068; A61F 2002/0072;
(Continued)

(56) References Cited

U.S. PATENT DOCUMENTS 3,444,024 A   5/1969   Hillas
5,593,441 A   1/1997   Lichtenstein et al.
(Continued)

FOREIGN PATENT DOCUMENTS

CN   1547489 A    11/2004
CN   101112335 A   1/2008
(Continued)

OTHER PUBLICATIONS

American College of Surgeons, Surgery News, vol. 7, No. 9, p. 5, Sep. 2011.
(Continued)

*Primary Examiner* — Wade Miles
*Assistant Examiner* — Kankindi Rwego

(57) ABSTRACT

A surgical implant (20) comprises a flexible, areal basic structure (22) having a first face and a second face and being provided with pores (26) extending from the first face to the second face. A barrier layer (24) having a first face and a second face is placed, with its second face, at the first face of the basic structure (2) and attached to the basic structure (22). The barrier layer (24) is deformed into at least part of the pores (26) where it forms, in a respective pore (10), a barrier region (28).

17 Claims, 2 Drawing Sheets

Figure 1:
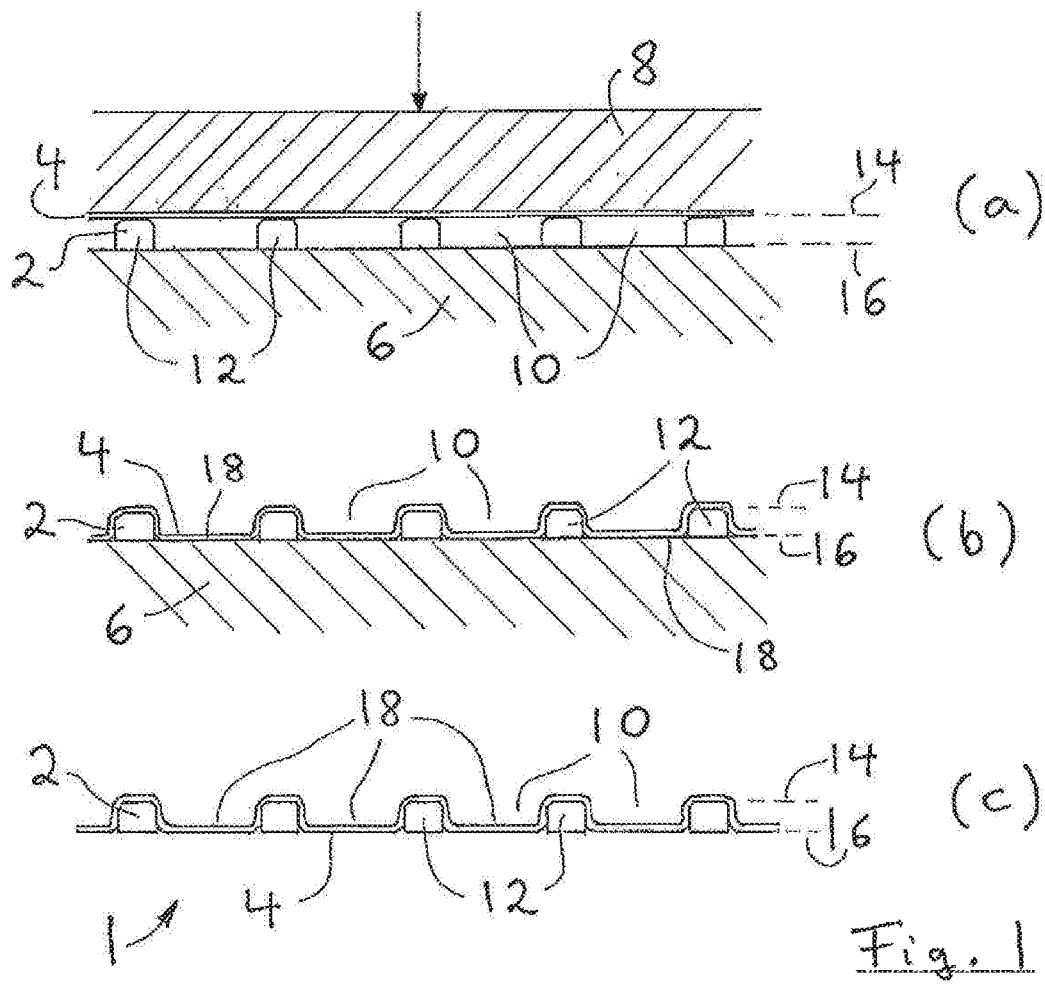

(51) Int. Cl.
*A61L 27/58* (2006.01)
*A61L 27/50* (2006.01)
*A61L 27/56* (2006.01)

(52) U.S. Cl.
CPC ....... *A61L 27/58* (2013.01); *A61F 2002/0072* (2013.01); *A61F 2210/0004* (2013.01); *A61F 2210/0076* (2013.01); *A61F 2240/00* (2013.01); *A61F 2250/0019* (2013.01); *A61F 2250/0023* (2013.01); *A61F 2250/0025* (2013.01); *A61F 2250/0026* (2013.01); *A61F 2250/0051* (2013.01); *A61F 2250/0097* (2013.01); *A61F 2310/00982* (2013.01); *A61F 2310/00994* (2013.01)

(58) Field of Classification Search
CPC ...... A61F 2002/0081; A61F 2002/0086; A61F 2002/009; A61F 2002/0091; A61F 2210/0004; A61F 2210/0076; A61F 2240/00; A61F 2250/0019; A61F 2250/0023; A61F 2250/0025; A61F 2250/0026; A61F 2250/0051; A61F 2250/0097; A61F 2310/00982; A61F 2310/00994; Y10T 428/24322; Y10T 428/24331; Y10T 428/24339; Y10T 428/24355; A61L 27/34; A61L 27/50; A61L 27/56; A61L 27/58
USPC ........................................................ 606/151
See application file for complete search history.

(56) References Cited

U.S. PATENT DOCUMENTS

| | | | |
|---|---|---|---|
| 7,615,065 | B2 | 11/2009 | Priewe et al. |
| 8,579,990 | B2 | 11/2013 | Priewe |
| 10,588,731 | B2 * | 3/2020 | Priewe .................. A61F 2/0063 |
| 2009/0157172 | A1 | 6/2009 | Kokate |
| 2011/0238153 | A1 | 9/2011 | Atanasoska |
| 2014/0257032 | A1 | 9/2014 | Hacker |
| 2014/0276999 | A1 | 9/2014 | Harms et al. |
| 2014/0343580 | A1 | 11/2014 | Priewe |
| 2015/0057762 | A1 | 2/2015 | Harms et al. |

FOREIGN PATENT DOCUMENTS

| | | |
|---|---|---|
| CN | 104220024 B | 6/2017 |
| CN | 104582633 | 1/2019 |
| EP | 1541183 B1 | 8/2009 |
| EP | 2379003 B1 | 10/2015 |
| EP | 2644161 B1 | 10/2017 |
| JP | 2014514941 A | 6/2014 |
| WO | 93/17635 A1 | 9/1993 |
| WO | 03041613 A1 | 5/2003 |
| WO | 2003/099160 A1 | 12/2003 |
| WO | 2010057632 A1 | 5/2010 |
| WO | 2013155174 A1 | 10/2013 |
| WO | 2015024659 A1 | 2/2015 |

OTHER PUBLICATIONS

ASIT Conference Book, Surgical Conference 2011: Cutlers' Hall, Sheffield, Apr. 15-17, p. 2.
International Search Report dated Dec. 20, 2016 for International Application No. PCT/US2016/055622.

* cited by examiner

SURGICAL IMPLANT AND PROCESS OF MANUFACTURING THEREOF

CROSS REFERENCE TO RELATED APPLICATION

This application is a continuation of co-pending U.S. application Ser. No. 15/259,227 filed Sep. 8, 2016, which claims priority from German Patent Application DE 10 2015 013 992.4 filed Oct. 30, 2015 the disclosure of which is hereby incorporated by reference in its entirety.

The invention relates to a surgical implant, in particular for repair of a tissue or muscle wall defect, such as a ventral hernia, and to a process of manufacturing such an implant.

Many ventral hernia repair implants comprise a surgical mesh and one or more adhesion barrier layers to prevent the adhesion of internal structures, like the intestine, to the mesh. For laparoscopic surgery, the surgeon has to roll the implant, pass it through a trocar sleeve and then lift it up with the mesh side facing to the abdominal wall (parietal side) and the adhesion barrier of the implant facing to the internal organs (viscera). Ideally, during the positioning of the mesh on the peritoneum, there is no need for an additional aid and the mesh sticks (clings) itself to the abdominal wall and can be easily fixated with clips or sutures to the abdominal wall.

The surgical implant Physiomesh® by Ethicon is a barrier/mesh composite implant which fulfils these optimal requirements. In Physiomesh®, a mesh layer is sandwiched between a barrier layer on the visceral side and an additional film for achieving a clinging effect on the parietal side.

U.S. Pat. No. 8,579,990 B discloses a mesh laminate comprising perforated polymer films on both sides of a surgical mesh. This surgical implant clings to the abdominal wall after laparoscopic placement, without the use of additional instruments.

WO 03/099160 A describes a surgical implant comprising a knobbed film, which can be connected to a mesh-like basic structure. The knobs of the film are manufactured in a step independent of a further step in which the knobbed film is attached to the basic structure. Generally, the knobs point away from the basic structure in order to minimize, by means of the knobs, adhesion effects, and it would be difficult to align the knobs with the mesh pores for fitting the knobs into the mesh pores.

The object of the invention is the provision of a surgical implant, in particular for repair of a tissue or muscle wall defect, which can be easily handled during placement, which has barrier properties on the visceral side, which requires a relatively small amount of material only, and which can be manufactured in an efficient manner. In particular, it would be desirable to be able to achieve a clinging effect on the parietal side without the need for an additional film, which would allow for tissue integration on the parietal side and minimize the amount of material used for the implant.

This object is achieved by the surgical implant according to claim 1. Claim 19 relates to a process of manufacturing such a surgical implant. Advantageous versions of the invention follow from the dependent claims.

The surgical implant according to the invention comprises a flexible, areal basic structure having a first face and a second face (i.e., a first side and a second side). The term "areal" means that the basic structure is generally flat, i.e. that it has a relatively small thickness, but because the basic structure is flexible it can be deformed into the third dimension. The basic structure is provided with pores extending from the first face to the second face. The surgical implant further comprises a barrier layer having a first face and a second face, which is placed, with its second face, at the first face of the basic structure and is attached to the basic structure. The barrier layer is deformed into at least part of the pores where it forms, in a respective pore, a barrier region. In a barrier region, the second face of the barrier layer may be closer to the second face of the basic structure than the first face of the barrier layer is to the first face of the basic structure.

The basic structure can be designed, e.g., as a surgical mesh, a mesh-like sheet, a spacer fabric, a perforated film, a perforated woven, a perforated non-woven, or as a mesh pouch (e.g. as a surgical mesh wherein part of the mesh is folded to form a pocket). An essential feature of the basic structure is the presence of pores which extend across the thickness of the basic structure. The pores may have a size, e.g., in the range of from 1 mm to 9 mm. Herein, the size of a given pore is defined as the greatest (free) width of that pore. It is also possible that the pores of a given basic structure have different sizes and/or different shapes. The barrier layer generally has an anti-adhesive effect and prevents bodily tissue from growing into the basic structure via the first face thereof. It can be made from an absorbable material so that these effects are temporarily, which permits a control of the healing process after implantation. Starting from the first face of the basic structure, the barrier layer enters at least part of the pores and then extends, in the inner area of a pore considered, e.g. roughly at the level of the second face of the basic structure or not far from that, to form a barrier region inside that pore. In this way, the second face may get largely smooth, because the structure determined by the second face of the basic structure may be generally leveled by the barrier regions formed by the barrier layer inside the pores of the basic structure.

In many cases, the basic structure does not have plane surfaces on a small-scale level, e.g. due to points where threads in a warp-knitted structure cross each other. Therefore, it may be more convenient to define the extent by which a barrier region in a pore of the basic structure approaches the second face of the basic structure in terms of a roughness which is averaged over a larger area of the surgical implant. To this end, a suitable measure is the average roughness, as defined in ASME B46.1-2009 (and similarly in DIN EN ISO 25178-2). In embodiments of the invention, the average roughness is measured over that area of the basic structure where the barrier layer is deformed into pores of the basic structure, and the average roughness is smaller at the second faces of the barrier layer and the basic structure than at the first faces of the barrier layer and the basic structure.

Specifically, the ratio of the average roughness measured at the second faces of the barrier layer and the basic structure to the average roughness measured at the first faces of the barrier layer and the basic structure has a value in one of the following ranges: 0.0-0.1, 0.1-0.2, 0.2-0.3, 0.3-0.4, 0.4-0.5, 0.5-0.6, 0.6-0.7, 0.7-0.8, 0.8-0.9, 0.9-1.0.

In Section 1-6.1 of ASME B46.1-2009, the average roughness $S_a$ is defined as $$S_a = (1/A_e) \iint |Z(x,y)| dx dy$$

The integration is performed over x and y (area integral) in that region of the basic structure where the barrier layer is deformed into pores of the basic structure. The total size of this area is $A_e$. That means, if the barrier layer extends over all of the basic structure and if the barrier layer deforms into all of the pores of the basic structure, $A_e$ is the area of the basic structure. $Z(x,y)$ is the function used to represent the point-by-point deviations between the measured topology and the mean surface (see 1-5.2 of ASME B46.1-2009; least squares mean surface). Z(x,y) varies between positive and negative values, for which reason its absolute value |Z(x,y)| is taken to characterize the roughness. The mean surface at the first faces of the barrier layer and the basic structure has to be determined independently of the mean surface at the second faces of the barrier layer and the basic structure.

Since the average roughness is smaller at the second faces of the barrier layer and the basic structure (i.e., measured from the side of the second faces) than at the first faces of the barrier layer and the basic structure (i.e., measured from the side of the first faces), the surgical implant is generally smoother at the side of the second faces.

In a laparoscopic repair procedure, the surgical implant according to the invention clings well to the abdominal wall or the peritoneum (parietal side) if the second faces of the basic structure and the barrier layer are oriented towards the peritoneum (and if a suitable material of the barrier layer is selected), because this second faces provide a large contact area. If required, the implant can be easily repositioned, and it can be fixated by using fixation means like sutures, clips or surgical tacks. The clinging properties facilitate the surgical procedure. At the first faces (visceral side), the barrier layer prevents adhesions. Thus, the surgical implant according to the invention provides or increases clinging properties to the peritoneum during laparoscopic repair, without the use of additional film material mounted at the second face of the basic structure (as in the prior art). The one barrier layer has a dual function: (1) adhesion barrier (visceral side) and (2) clinging aid (parietal side). The contact area on the parietal side is increased without affecting the mesh-to-tissue contact area, in contrast to prior-art implants comprising a full film layer at the parietal side. As the parietal side of the implant is not covered by such an additional film layer, tissue integration from the parietal side is generally possible. Moreover, since the barrier layer is deformed into the pores of the basic structure, it can be strongly attached to the basic structure.

Thus, in an example for a process of intraperitoneally placing the surgical implant according to the invention in a patient's body, the surgical implant is introduced into the body via a trocar sleeve and is deployed, the second face of the basic structure facing the patient's peritoneum. Then the surgical implant clings to the peritoneum, generally without additional holding aids, and it can be fixed on the peritoneum, e.g. by sutures, clips and/or surgical tacks. The implant can be used in open surgery as well.

The surgical implant according to the invention can be applied, e.g., for repair of a tissue or muscle wall defect, such as a ventral hernia, but also as a hernia mesh in general, as a pelvic mesh, as a breast implant support, as a patch for the dura mater, or as a reinforcement for staple lines or suture lines in general surgery.

Another advantage of the surgical implant according to the invention is an easy and efficient way of manufacturing, see below.

In the pores of the basic structure comprising a region of the barrier layer, this barrier region may be basically flat. Such a design contributes to the smoothness of the second face in the surgical implant, as mentioned above. For example, deviations from ideal flatness (i.e. flat like a plane) may result in a ripple of less than 50 μm or less than 30 μm or less than 20 μm, which feels generally smooth in palpation. The barrier region may have a size (defined as the greatest width of that basically flat barrier region in the pore contemplated) in the range of, e.g., from 0.5 mm to 5 mm, depending on the size of the respective pore of the basic structure. The size of the barrier region is less or slightly less than the respective pore size because the barrier layer, from the edges of the barrier region, rises or steeply rises in order to cover the material of the basic structure at the first face of the basic structure.

The angle between a barrier region and a plane in parallel to the second face of the basic structure may be, e.g., in the range of from 00 to 50. When approaching the edges of the pore in question, the slope changes because the barrier layer has to adjust to the geometry of the basic structure. In such regions, typical values for the slope are, e.g., in the range of from 8° to 110°, or of from 10° to 50°.

Between pores of the basic structure, the barrier layer may form ridges where the first face of the barrier layer rises above the first face of the barrier layer in an adjacent barrier region by an amount in the range of, e.g. from 50 μm to 900 μm. In this way, the first face of the implant (i.e., the barrier layer side) can feel rougher than the second face by palpation. These ridges may aid in an anti-adhesive effect of the barrier layer.

The barrier layer may be provided with pores having a smaller size than that of the pores of the basic structure.

Generally, the barrier layer may be continuous, in particular consisting of one piece of material, or it may be made of a plurality of spaced film pieces, e.g. of film pieces which do not touch each other or which touch just in common corners. However, each film piece would be continuous over at least two or more pores of the basic structure. Generally, the barrier layer extends over material of the basic structure (at the first face of the basic structure) and is not restricted to zones just inside the pores.

In order to fix the barrier layer to the basic structure, a bonding material can be used which has a melting temperature lower than the melting temperature of at least part of the material of the basic structure and lower than the melting temperature of at least part of the material of the barrier layer. Depending on the materials of the basic structure and of the barrier layer, a suitable bonding material may comprise poly-p-dioxanone, which is absorbable. The bonding material can be embodied, e.g., as filaments incorporated in threads used for warp-knitting the basic structure, as threads of the basic structure, or as a film layer arranged between the basic structure and the barrier layer during the shaping of the barrier layer (see below). In the process, the temperature is adjusted such that the bonding material gets soft and sticky to serve as a glue, while the basic structure and the barrier layer are not misshaped in an uncontrolled way.

In advantageous embodiments of the invention, the basic structure is long-term stable. This can be achieved by nonabsorbable materials, which generally are well known in the art. Examples of non-absorbable materials are polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyimides, polyurethanes, polyisoprenes, polystyrenes, polysilicones, polycarbonates, polyaryletherketones, polymethacrylic acid esters, polyacrylic acid esters, aliphatic polyesters, aromatic polyesters, and mixtures of such substances as well as copolymers of polymerizable substances of that list.

The basic structure may also comprise absorbable material or slowly absorbable material (i.e. material which, 90 days after implantation, still has at least 10% of its initial tensile strength), either exclusively or in addition to nonabsorbable material, e.g. synthetic bioabsorbable polymer materials, polyhydroxy acids, polylactides, polyglycolides, copolymers of glycolide and lactide, copolymers of glycolide and lactide in the ratio 90:10, copolymers of glycolide and lactide in the ratio 5:95, copolymers of lactide and trimethylene carbonate, copolymers of glycolide, lactide and trimethylene carbonate, polyhydroxybutyrates, polyhydroxyvaleriates, polycaprolactones, copolymers of glycolide and ε-caprolactone, polydioxanones, poly-p-dioxanone, synthetic and natural oligo- and polyamino acids, polyphosphazenes, polyanhydrides, polyorthoesters, polyphosphates, polyphosphonates, polyalcohols, polysaccharides, polyethers, collagen, gelatin, bioabsorbable gel films cross-linked with omega 3 fatty acids, oxygenized regenerated cellulose, or mixtures of such substances.

The barrier layer may be designed as a polymeric film and may comprise an absorbable material, e.g. copolymers of glycolide and ε-caprolactone, collagens, gelatine, hyaluronic acid, polyvinyl pyrrolidone, polyvinyl alcohol, fatty acids, polyhydroxy acids, polyether esters, polydioxanones, or mixtures or copolymers of polymerizable substances thereof. However, a non-absorbable material of the barrier layer (or a mixture of absorbable and non-absorbable materials) is conceivable as well. The barrier layer may be transparent. Non-transparent embodiments of the barrier layer are also possible.

As already mentioned, the barrier layer generally has an anti-adhesive effect and prevents bodily tissue from growing into the basic structure via the first face thereof. As an anti-adhesive layer, it prevents or minimizes adhesion to internal body structures such as bowel, liver or spleen to the implant. Suitable films can be made from resorbable materials, for example comprising poly-p-dioxanone (PDS®, Ethicon), copolymers of glycolide and ε-caprolactone (e.g., MONOCRYL® (poliglecaprone 25), Ethicon) and/or copolymers of glycolide and lactide (in particular in the ratio 90:10; VICRYL® (poly-glactin 910), Ethicon). Generally, a large variety of synthetic bioabsorbable polymer materials can be used, for example polyhydroxy acids (e.g., polylactides, polyglycolides, polyhydroxybutyrates, polyhydroxyvaleriates), polycaprolactones, polydioxanones, and PEG- or PEO-esters thereof such as PLGA-PEG-PLGA or Methoxypolyethyleneglycol-PLGA, synthetic (but also natural) oligo- and polyamino acids, polyphosphazenes, polyanhydrides, polyorthoesters, polyphosphates, polyphosphonates, polyalcohols, polysaccharides, polyethers, polycyanoacrylates (poly 2-OCA-co-BLCA) as cured from Ethicon's Omnex®. However, naturally occurring materials such as fibrin, albumin, collagens and gelatine, hyaluronic acid or naturally derived materials such as bioabsorbable gel films or gel forming films, cross-linked omega 3-fatty acids or oxygenized regenerated cellulose (ORC), crosslinked albumines or rh albumines where an albumin solution is cross-linked and foamed/expanded, crosslinked products where polyethylene glycol (PEG) ester solution and a trilysine amine are cross-linked, are possible as well. Examples for non-resorbable materials are PTFE sheet, fluorinated polyolefine (PVDF), copolymers of vinylidene fluoride and hexafluoropropene, silicone, durable polyvinyl alcohol gels, polyurethane.

It is also possible that the barrier layer comprises, at least in part, swelling or gel-forming substances. Such substances include surfactants such as PPO-PEO block copolymers (polox-amers), polysorbates, sorbitan esters (like sorbitan monolaurate, sorbitan monopalmitate, sorbitan monostearate, sorbitan tristearate, sorbitan monooleate), phospholipids, hydophilic natural or synthetic polymers such as alginate, dextrane, chitosane, carracen, polyethylene glycol (PEG), sol-uble polyvinylalcohol (PVA), polyvinylpyrrolidone (PVP), car-boxymethyl cellulose (CMC), HES (hydroxyethyl starch). Hydro-gel-forming polymers may be obtained upon polymerization or polyaddition or polycondensation containing at least one of the substances selected from the following group: polymerized hydroxyethyl methacrylate (HEMA), polymerized hydroxypropyl methacrylate (HPMA), polymerized α-methacryloyl-ω-methoxy polyethylene glycol, polymerized methacryloyloxyethyl phosphory-lcholine (MPC), polyethylene glycol-bisacrylate and copolymers thereof, cured resorbable pre-polymers of type A-B-C-B-A with commercial examples sold as Focalseal® (Genzyme) or Advaseal® (Ethicon) with A=acryl or methacryl groups, B=hydrolyti-cally splittable groups containing polymers of lactide, glycolide, 2-hydroxybutyric acid, 2-hydroxyvaleriac acid, trimethylene carbonate, polyorthoesters, polyanhydrides, polyphosphates, polyphosphazenes and/or polyamides and/or copolymers thereof, and C=hydrophilic polymers, in particular polyethylene glycol (PEG), polyvinyl alcohol (PVA), polyvinyl pyrrolidone (PVP), poly-N-isopropylacrylamide (PNiPAAM).

Moreover, the surgical implant according to the invention may comprise at least one active ingredient and/or at least one contrast agent, e.g. incorporated in, applied to or adsorbed to the basic structure and/or provided at a layer of the implant, e.g. incorporated in or adsorbed to the barrier layer, and/or in encapsulated form.

Examples for active ingredients are biologically active or therapeutic ingredients which can optionally be released locally after the implantation. Substances which are suitable as active or therapeutic agents may be naturally occurring or synthetic, and include but are not limited to, for example, antibiotics, antimicrobials, antibacterials, antiseptics, chemotherapeutics, cytostatics, metastasis inhibitors, antidiabetics, antimycotics, gynecological agents, urological agents, anti-allergic agents, sexual hormones, sexual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, cells occurring naturally in the body or genetically modified cells. The active or therapeutic agent may be present in various forms including in an encapsulated form or in an adsorbed form. With such active agents, the patient outcome may be improved or a therapeutic effect may be provided (e.g., better wound healing, or inflammation inhibition or reduction).

One preferred class of active agents are antibiotics that include such agents as gentamicin or ZEVTERA™ (ceftobiprole medocaril) brand antibiotic (available from Basilea Pharmaceutica Ltd., Basel, Switzerland). Other active agents that may be used are highly effective broad-band antimicrobials against different bacteria and yeast (even in the presence of bodily liquids) such as octenidine, octenidine dihydrochloride (available as active ingredient in Octenisept® disinfectant from Schilke & Mayer, Norderstedt, Germany), polyhexamethylene biguanide (PHMB) (available as active ingredient in Lavasept® from Braun, Switzerland), triclosan, copper (Cu), silver (Ag), nanosilver, gold (Au), selenium (Se), gallium (Ga), taurolidine, N-chlorotaurine, alcohol-based antiseptics such as Listerine® mouthwash, N-a-lauryl-L-arginine ethyl ester (LAE), myristamidopropyl dimethylamine (MAPD, available as an active ingredient in SCHERCODINE™ M), oleamidopropyl dimethylamine (OAPD, available as an active ingredient in SCHERCODINE™ O), and stearamidopropyl dimethylamine (SAPD, available as an active ingredient in SCHERCO-DINE™ S), fatty acid monoesters, taurolidine, and PHMB.

Another class of active agents are local anesthetics that include such agents as: Ambucaine, Benzocaine, Butacaine, Procaine/Benzocaine, Chloroprocaine, Cocaine, Cyclomethycaine, Dimethocaine/Larocaine, Etidocaine, Hydroxyprocaine, Hexylcaine, Isobucaine, Paraethoxycaine, Piperocaine, Procainamide, Propoxycaine, Procaine/Novocaine, Proparacaine, Tetracaine/Amethocaine, Lidocaine, Articaine, Bupivacaine, Dibucaine, Cinchocaine/Dibucaine, Etidocaine, Levobupivacaine, Lidocaine/Lignocaine, Mepivacaine, Metabutoxycaine, Piridocaine, Prilocaine, Propoxycaine, Pyrrocaine, Ropivacaine, Tetracaine, Trimecaine, Tolycaine, combinations thereof, e.g., Lidocaine/prilocaine (EMLA) or naturally derived local anesthetics including Saxitoxin, Tetrodotoxin, Menthol, Eugenol and prodrugs or derivatives thereof.

Moreover, a contrast agent may be included in or on the surgical implant according to the invention. Such a contrast agent may be a gas or gas-creating substance for ultrasound contrast or for MRI contrast, such as metal complexes like GdDTPA or superparamagnetic nanoparticles (Resovist™ or Endorem™) as taught in EP 1 324 783 B1, which is incorporated by reference. X-Ray visible substances might be included as shown in EP 1 251 794 B1 (incorporated by reference), including pure zirconium dioxide, stabilized zirconium dioxide, zirconium nitride, zirconium carbide, tantalum, tantalum pentoxide, barium sulphate, silver, silver iodide, gold, platinum, palladium, iridium, copper, ferric oxides, not very magnetic implant steels, non-magnetic implant steels, titanium, alkali iodides, iodated aromatics, iodated aliphatics, iodated oligomers, iodated polymers, alloys of substances thereof capable of being alloyed.

The surgical implant according to the invention may also comprise an orientation marker adapted for distinguishing the first face of the basic structure from the second face of the basic structure. Such an orientation marker can be made, e.g., from an absorbable poly-p-dioxanone film dyed with the violet dye "D&C Violet No. 2" and laminated to, e.g., the visceral side of the barrier layer (i.e., the first face of the barrier layer), which preferably is not dyed. If the orientation marker has an appropriate asymmetric shape, it will be easily visible whether the implant is oriented correctly, with the barrier layer facing the internal organs, or whether not. Alternatively, the orientation marker (or parts therof) may be arranged at the second face of the barrier layer, i.e. in between the basic structure and the barrier layer.

In other embodiments, printing or spraying techniques are used to apply the marker to the barrier layer. For example, a coloring agent may be prepared by dissolving a dye and a polymer in a suitable solvent, and then the marker is sprayed onto the outer face of the barrier layer, e.g. by using an air-brush technique or an ink-jet printer. After evaporation of the solvent, the marker is firmly connected to the barrier layer.

Alternatively, the marker may be applied to the parietal side of the basic structure (i.e., the second face of the basic structure). In this case, the clinging effect due to the barrier layer being deformed into the pores of the basic structure will not be significantly affected if the marker is relatively small or flat.

In an advantageous embodiment, the surgical implant comprises a basic structure designed as a macro-porous surgical mesh (about 1 mm to 9 mm maximum extension within each pore) knitted from polypropylene (PROLENE®, Ethicon; non-absorbable) and poly-p-dioxanone (PDS®, Ethicon; absorbable) fibers. An absorbable film made of a copolymer of glycolide and ecaprolactone (MONOCRYL® (poliglecaprone 25) suture polymer, Ethicon) is laminated to the first face of the basic structure, wherein it extends into the pores and serves as the barrier layer. Additionally, an orientation marker cut from a dyed poly-p-dioxanone film is fixed to the barrier layer. The implant is generally flat and has a "mesh side" and a "film side".

The surgical implant of this specific embodiment is a partially absorbable, flexible composite mesh prosthesis intended for the repair of ventral or incisional hernias and other fascial defects, including inguinal hernias. The implant can be placed in an IPOM (intra-peritoneal onlay mesh) technique. After intra-peritoneal implantation, the implant is in a permanent tissue contact. It comes into contact with the peritoneum on the parietal side and with intra-abdominal organs on the visceral side. In summary, the structural elements of the implant have the following functions: (1) The non-absorbable polypropylene mesh component of the basic structure is used to reinforce or bridge defects to provide extended support during and following wound healing. (2) The absorbable barrier layer of MONOCRYL® is intended to physically separate the basic structure from underlying tissue and organ surfaces (as bowel/omentum) during the critical wound healing period until the basic structure mesh is covered by a neoperitoneum, thereby reducing the extent and severity of unintended tissue attachment to the permanent material of the basic structure. (3) And during laparoscopic placement, the textured pattern formed at the second face of the basic structure by the mesh structure and by the regions of the barrier layer deformed into the mesh pores provides good clinging properties so that the handling of the implant is much improved.

In a process of manufacturing the surgical implant according to the invention, a flexible, areal basic structure having a first face and a second face is provided, with pores extending from the first face to the second face. Moreover, a barrier layer having a first face and a second face is provided. The basic structure is placed onto a hard support, the second face of the basic structure facing the support. The barrier layer, with its second face, is placed onto the first face of the basic structure. A pad is placed onto the barrier layer (i.e., onto its first face), wherein the pad is softer than the support. Then, heat and pressure are applied, thereby softening the material of the barrier layer, urging it into the pores of the basic structure, and attaching the barrier layer to the basic structure. Afterwards, optionally not before the end of a preselected period of time, the temperature and pressure can be decreased. It is also possible to cool (e.g. actively or by waiting) the support and/or the pad, e.g. to a preselected temperature or for a preselected period of time, while the pressure is at least partially maintained, and decrease the pressure afterwards.

This process is very efficient because the barrier layer is textured and laminated with the basic structure in just one step, wherein material of the barrier layer enters into the pores of the basic structure and is connected to the basic structure at the same time. Thus, any problems related to the matching of a pre-shaped barrier layer into the pores of the basic structure do not occur. The softer pad presses the material of the barrier layer into the pores and is depressed itself in areas where material of the basic structure is present. Thus, the softer pad adjusts to the pore pattern of the basic structure. On the opposite side, the hard support ensures a largely smooth surface of the implant. Generally, all variants of the surgical implant according to the invention explained above, including those defined in terms of average roughness, may be manufactured by this process.

To improve the attachment between the barrier layer and the basic structure, a bonding material can be used, which has a melting temperature lower than the melting temperature of at least part of the material of the basic structure and lower than the melting temperature of at least part of the material of the barrier layer. Such a bonding material melts or gets soft during the application of heat and pressure, thus acting as a kind of melt glue, whereas the basic structure and the barrier sheet are still able to keep their desired shapes.

The bonding material may be included in the basic structure provided, e.g. in the form of filaments comprising poly-p-dioxanone. Alternatively (or additionally), the bonding material may be included in the barrier layer provided, e.g. as a sub-layer comprising poly-p-dioxanone and laminated to a sublayer comprising barrier material having a higher melting point than poly-p-dioxanone.

When the above-referenced advantageous embodiment of the surgical implant is manufactured, in which the basic structure is knitted from polypropylene and from poly-p-dioxanone fibers, the poly-p-dioxanone fibers serve as the bonding material. The basic structure can be knitted in a way that it is still a stable polypropylene mesh after the poly-p-dioxanone component has lost its shape and structural function during the manufacturing process (and after it has been absorbed after implantation).

After applying heat and before the pressure is (completely) relieved, the basic structure and the barrier layer may be cooled (actively or by waiting), e.g. via the support and/or the pad, as already mentioned above. In this way, the barrier layer is "frozen" in its desired shape and any bonding material can settle or harden so that the surgical implant acquires and keeps its final design.

In another process of manufacturing the surgical implant according to the invention, the barrier layer is adhered to the basic structure by using a pressure-sensitive adhesive, without applying heat. In this case, pressure can be exerted in a press between a hard support and a softer pad, wherein the pad urges the barrier layer into the pores of the basic structure (as in the former process) and the pressure also results in a good adhesion of the barrier layer to the basic structure.

In the following, the invention is further explained by means of examples. The drawings show in FIG. 1 a schematic illustration of an embodiment of the process of manufacturing a surgical implant according to the invention, in longitudinal sections, i.e. in part (a) an arrangement of a basic structure and a barrier layer placed in a set-up comprising a hard support and a soft pad, in part (b) the arrangement of part (a) after exerting pressure and elevated temperature and after removing the soft pad, and in part (c) the surgical implant taken from the support, FIG. 2 an exploded three-dimensional view of an embodiment of the surgical implant according to the invention, FIG. 3 in parts (a) and (b) three-dimensional scanning microscopic images of two embodiments of the surgical implant according to the invention, which differ slightly due to manufacturing conditions, seen from the side where a film (barrier layer) is attached, and FIG. 4 a schematic depth profile contour map of the embodiment according to FIG. 3(*a*).

The structure of the surgical implant according to the invention can be best understood by means of an example illustrating a manufacturing process of the implant, see FIG. 1 in which the finished surgical implant is designated by reference numeral 1. FIG. 1 shows schematic views in longitudinal section.

In FIG. 1(*a*), an arrangement of a basic structure 2 and a barrier layer 4 is placed between a hard support 6 and a pad 8, which is softer than the support 6.

The basic structure 2 may be designed as, e.g., a surgical mesh or a mesh-like sheet. In any case, it is areal (i.e. generally flat) and flexible. In FIG. 1, the dimension of the area of the basic structure 2 not shown in the figure extends perpendicularly to the plane of the paper. Moreover, the basic structure 2 comprises pores 10 surrounded by material 12. The pores 10 extend from a first face (side) 14 to a second face (side) 16 of the basic structure 2. In the embodiment, the basic structure 2 is designed as a mesh-like sheet (made, e.g., by injection-molding or laser-cutting of polymeric films) so that the first face 14 and the second face 16 are essentially plan. If the basic structure is, e.g., a warp-knitted or crocheted surgical mesh, the material 12 will be provided by filaments (monofilaments and/or multifilaments), and the first face 14 and the second face 16 will be somewhat rougher because of the intersections of the filaments.

In the embodiment, the barrier layer 4 is made from a thin absorbable film without pores. In other embodiments, the barrier layer may comprise pores, which are generally smaller than the pores 10 of the basic structure 2, however. According to FIG. 1(*a*), the barrier layer 4 is placed onto one side of the basic structure 2, which by definition is the first face 14.

In the manufacturing process, the arrangement of the basic structure 2 and the barrier layer 4 is heated and submitted to external pressure, as indicated by the arrow in FIG. 1(*a*). The materials of the basic structure 2 and the barrier layer 4 are appropriately selected such that the basic structure 2 essentially keeps its shape while the material of the barrier layer 4 get soft enough at the raised temperature so that it is urged, by the relatively soft pad 8, into the pores 10 of the basic structure 2. Examples including more precise information on the materials and the processing conditions are given further below. The soft pad 8 largely adapts to the depressions provided by the pores 10, while the support 6 defines a plane at the level of the second face 16 of the basic structure 2 which is not traversed by the material of the barrier layer 4.

FIG. 1(*b*) shows the result after the arrangement has been cooled to room temperature and the pad 8 has been removed. Inside the pores 10, the barrier layer 4 forms barrier regions 18, which are largely plane and have their outer face located (within tolerances due to the manufacturing process and the initial surface roughness of the basic structure 2) at the level of the second face 16 of the basic structure 2. At the edge zones of a given barrier region 18, the barrier layer 4 rises, assuming a rather steep slope, and adjusts to the shape provided by the basic structure 2. The areas of the barrier layer 4 emerging from adjacent pores 10 are connected to each other at the level of the first face 14 so that the barrier layer 4 is coherent and able to fulfill its barrier function. FIG. 1(*c*) displays the finished surgical implant 1 when taken away from the support 6.

Figure 2:
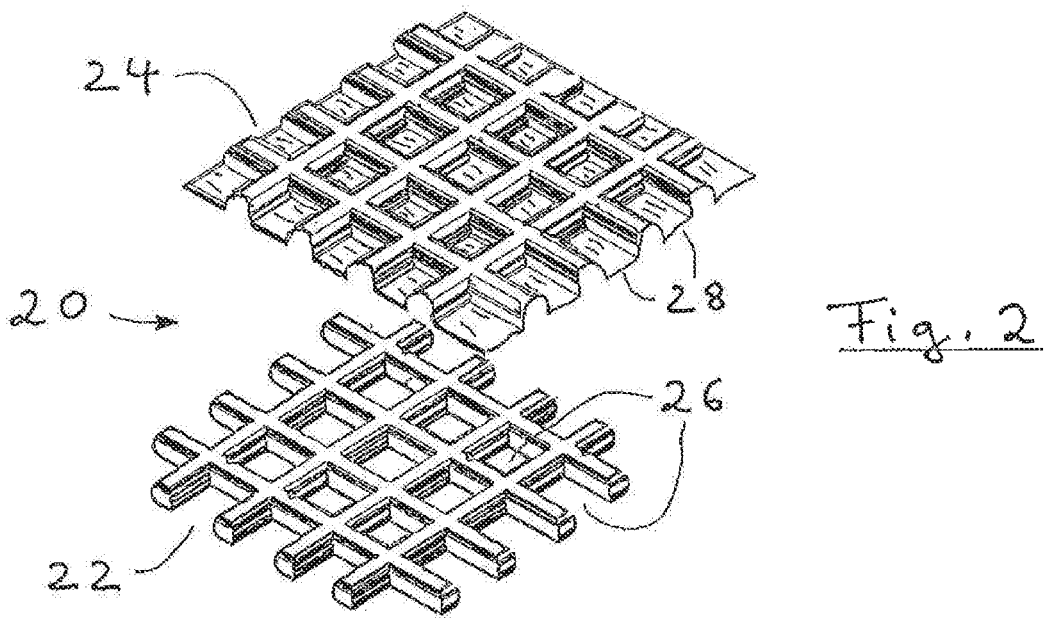

FIG. 2 is an exploded three-dimensional view of an embodiment of the surgical implant, here designated by 20. The surgical implant 20 may be the surgical implant manufactured as explained by means of FIG. 1. It comprises a basic structure 22 designed, in the embodiment, as a flexible mesh-like sheet, and a barrier layer 24. It is well visible in FIG. 2 how the deformed regions of the barrier layer 24 fit into pores 26 of the basic structure 22. In FIG. 2, the barrier regions in the individual pores 26 are designated by 28.

To improve the adherence of the barrier layer to the basic structure, a bonding material can be used, which has a melting temperature lower than the melting temperature of at least part of the material of the basic structure and lower than the melting temperature of at least part of the material of the barrier layer. In the manufacturing process, the bonding material melts or gets very soft so that it acts as a kind of melt glue connecting the barrier layer to the basic structure. The bonding material may be incorporated in the basic structure and/or the barrier layer, see also the following examples.

EXAMPLE 1

A large-pored composite mesh of polypropylene monofilament fibers and poly-p-dioxanone (PDS®) monofilament fibers serving as a basic structure was placed on a tenter frame form on top of a hard support surface. An approximately 10 µm thick film of MONOCRYL® (see above) serving as a barrier layer was placed on top of the basic structure, followed by a soft silicone foam pad covered by a metal plate. This assembly was placed in a hot press at 10 bar heated up to 120° C. for a couple of minutes and cooled down at the same pressure. Under these conditions, the poly-p-dioxanone fibers of the basic structure acted as a melt glue to attach the barrier layer to the basic structure.

The barrier layer entered the pores of the basic structure, as described above (FIG. 1). Typical dimensions in the pore area of the surgical implant obtained in this way were: pore diameter (clear width) 1.71 mm, pore diameter (width measured between the centers of the mesh filaments defining the pore) 2.47 mm, diameter of largely flat barrier region in the pore 1.53 mm (about 90% of pore diameter).

In an optional second step, a marker cut from a thick film (150 µm) of violet poly-p-dioxanone was heat-laminated on top of the barrier layer in order to enable an easy distinction of both faces of the implant.

In a marker-free area, the thickness of this surgical implant was mechanically determined to be about 340 µm, about 10 µm thereof contributing to the film. The depressions in the pores forming the barrier regions had a depth, measured from the side of the first face (see FIG. 1) of up to 270 µm (when measured down from maxima due to raised structures like knots of the mesh), with an average depression depth of about 60% of the thickness of the implant. When seen from the other side, i.e. the side of the second face, some fibers and knots of the basic structure where exposed beyond the second face of the film layer by up to about 185 µm.

The average roughness $S_a$, defined as explained in detail further above, of both sides of the implant was determined by means of an optical scanning microscope of the type "Keyence Macroscope VR-3200" using standard settings adapted to measure the average roughness. On the side of the first face (film side, visceral side), the average roughness was 49 µm; on the side of the second face (mesh side, parietal side), it was 28 µm. For both sides, the mean surfaces were determined independently of each other. Thus, on the parietal side, the implant was considerably smoother, in spite of the fibers and knots emerging relatively far from the second face of the film layer. Generally, these fibers and knots are relatively small structures and do not contribute much to the average roughness as defined above.

An oval test article of about 15 cm×10 cm was cut from this surgical implant and was intraperitonially placed in a pig, with the second face, i.e. the side on which the filaments of the basic structure were exposed (reference numeral 16 in FIG. 1(*c*)), facing to the peritoneum. The implant easily attached to the peritoneum, holding its own weight including a marker, but could be repositioned and placed at different locations (more centrally and more laterally) without problems. The area weight of this test article was 68 g/m².

EXAMPLE 2

A surgical mesh of polypropylene filaments (basic mesh of Physiomesh® hernia repair implant of Ethicon, i.e. Physiomesh® without MONOCRYL® film) serving as a basic structure was placed on a supported hard silicon film covered by a baking paper in a form having pins for mesh fixation. After a corona treatment of the polypropylene mesh, a pre-laminate containing an 8-µm PDS® film (serving as melt glue) and a 20-µm MONOCRYL® film (serving as barrier layer) was placed on the mesh, with the PDS® side facing to the mesh. This assembly was covered with a soft silicone pad, and the form was closed with a metal plate. After a heat lamination step in a press at 120° C. for 5 minutes, the assembly was taken out of the press, cooled down between two cold metal plates for about 20 minutes, and finally taken out of the form.

In the resulting surgical implant, the MONOCRYL® film had assumed a mesh-like texture, as determined by the basic structure, with basically flat barrier regions in the respective pores having a width of about 1.5 mm and a depth (measured from the first face 14, see FIG. 1(*c*)) of about 200 µm to 230 µm.

The average roughness $S_a$ (see Example 1) of this surgical implant was 44 µm on the film side and 37 µm on the mesh side.

EXAMPLE 3

A TiO₂Mesh™ of Biocer GmbH (large-pored mesh warp-knitted from polypropylene monofilaments having their surface coated with titan dioxide) serving as a basic structure was covered with a pre-laminate composed of a 5-µm PDS® film (serving as a melt-glue) and a 20-µm MONOCRYL® film serving as a barrier layer, with the PDS® film side facing to the mesh. Any further surface treatment was not performed. This assembly was placed between a baking paper (mesh side) and a soft pad (film side) in a heat press at 10 bar, heated up to 120° C. for several minutes and cooled down under pressure to about 50° C.

After removing the surgical implant obtained in this way from the press, it was macroscopically evaluated. The film side felt rough and the mesh side felt smooth. Mesh and film were firmly connected to each other. On the film side, the topography of the film followed the essentially drop-like shape of the mesh pores, with flat barrier regions essentially filling the pores completely.

The surgical implant had a total thickness (mechanically determined) of 556 µm. The basically flat barrier regions of the film were located at a depth of up to 487 µm. The areal weight of the surgical implant was 90 g/m².

When placed at an abdominal wall with the mesh side facing the abdominal wall, the clinging effect of this surgical implant is due not only to the barrier regions in the pores, but also to the hydrophilicity of the TiO₂ coating of the mesh. In a test with a moist peritoneum of a pig, the implant adhered good enough to hold its own weight.

Figure 3:
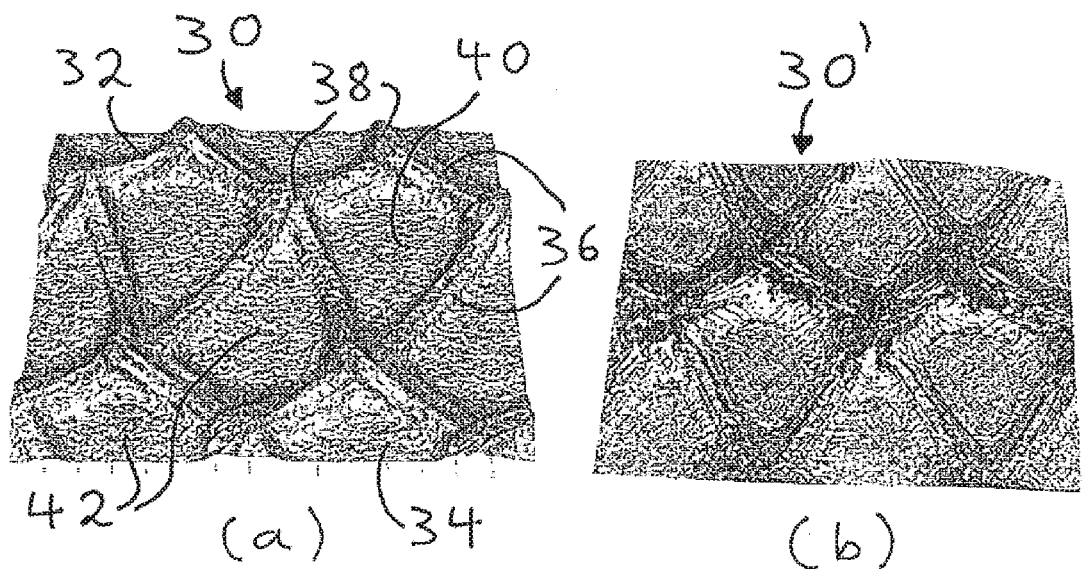

FIG. 3(*a*) shows a close-up three-dimensional view of the surgical implant (designated by reference numeral 30)

manufactured as described above, taken by a scanning microscope from the film side (first face 14 according to FIG. 1(*c*)). The shape of the basic structure 32 is clearly visible because the barrier layer 34 closely attaches to the filaments 36 of the basic structure 32. Since the basic structure 32 is warp-knitted, points 38 of intersecting filaments form peaks. In the pores 40, barrier regions 42 of the barrier layer 34 located generally at the level of the other side of the basic structure 32 (second face 16 according to FIG. 1(*c*)) are relatively large, filling most of the area of a respective pore 40.

A surgical implant 30' shown in FIG. 3(*b*) was manufactured in almost the same way as the surgical implant 30 of FIG. 3(*a*), the manufacturing conditions being only slightly different. Since a baking paper was not used, the barrier regions were slightly smoother. And since the pressure was somewhat lower, the barrier layer did not approach the sides of the filaments as closely as in the example according to FIG. 3(*a*).

The average roughness $S_a$ (see Example 1) of the surgical implant 30 (FIG. 3(*a*)) was 79 μm on the film side and 48 μm on the mesh side. For the implant 30' (FIG. 3(*b*)), it was 83 μm on the film side and 60 μm on the mesh side.

In surgical test procedures with pigs, both implants 30 and 30' adhered to the peritoneum.

Figure 4:
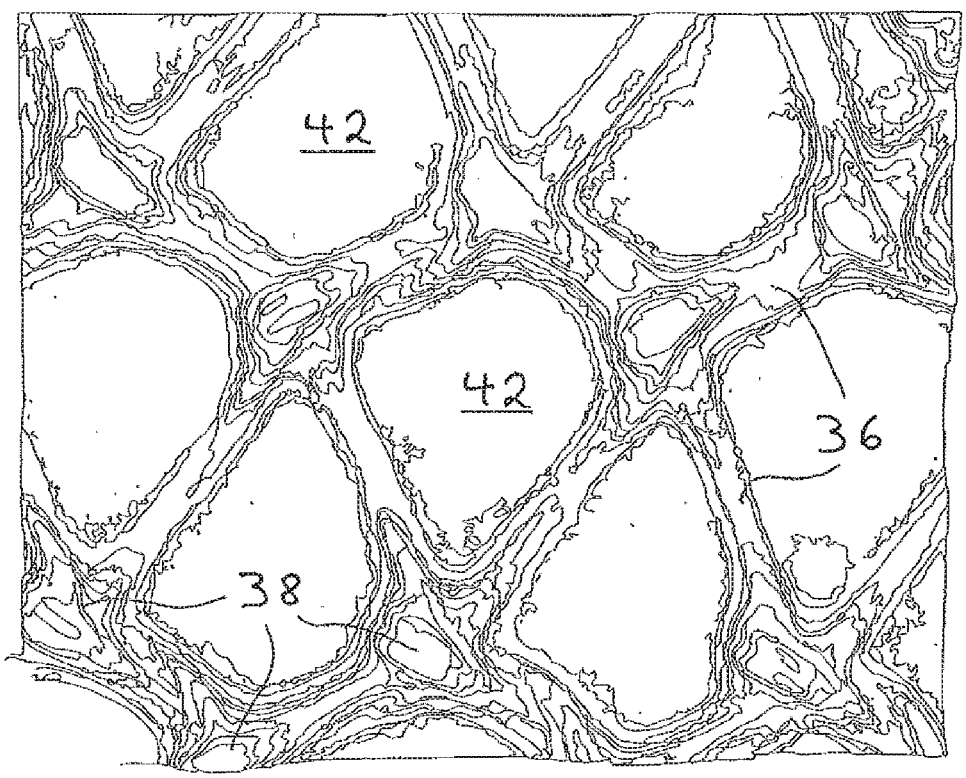

FIG. 4 is a depth profile contour map of the surgical implant according to FIG. 3(*a*).

EXAMPLE 4

Omyra® Mesh (B. Braun), an orientated cPTFE film having multiple pores in the mm range, as a basic structure was coronatreated on one side in order to render the surface acceptable for lamination and was covered with a prelaminate composed of a 5-μm PDS® film and a 20-μm MONOCRYL® film with the PDS® film side facing to the cPTFE film, the MONOCRYL® film serving as a barrier layer and the PDS® film serving as a bonding material. The assembly was placed between a hard pad (metal plate covered by baking paper on the cPTFE side) and a soft pad (MONOCRYL® film side) in a heat press at 10 bar, heated up to 120° C. and cooled down under pressure to about 50° C. After taking the surgical implant obtained in this way out of the press, the barrier layer was dimpled.

Laser scan microscopic evaluation showed film depressions of up to 178 μm and a total implant thickness of 201 μm, which means that the barrier layer film having a thickness of about 20 μm was completely impressed into the pores of the basic structure. Backside measurement demonstrated that the cPTFE struts, i.e. the material between the pores, were almost within the basically flat barrier regions of MONOCRYL®. Starting from such a barrier region, the out-of-plane angles of the barrier layer increased when approaching the struts, depending on the location within the pore, e.g. from about 35° to 39° and up to 48° or, in narrow sections of the pore, being in the order of 12° to 14°. The largely flat barrier regions in the central area of a pore had small out-of-plane angles, in the order of less than 10, and a typical size of 0.9 mm.

The average roughness $S_a$ (see Example 1) of this surgical implant was 48 μm on the film side and 24 μm on the side of the basic structure.

In a test, this implant was placed at a moist peritoneum of a pig, with the cPTFE side facing the peritoneum. In spite of the general hydrophobicity of PTFE, the adhesion forces between the peritoneum and the implant were large enough to hold the weight of the implant (245 g/m²), due to the clinging effect of the barrier regions of the barrier layer.

EXAMPLE 5

Samples of a surgical implant comparable to that of Example 1 were prepared in a rectangular size of 3 cm×5 cm with slightly rounded edges. Additionally, a circular dyed (violet) PDS® film disk of about 150 μm thickness was laminated centrally on top of the barrier layer of an implant.

Using samples of this implant, a rabbit peritoneal defect model was applied, as described in U.S. Pat. No. 8,629,314 B. Adhesion was evaluated after 2 weeks, see Table 1.

When a sample was correctly placed, with the smooth mesh side (second face 16 in FIG. 1(*c*)) to the abdominal wall and the ridged (rough) barrier layer side (first face 14 in FIG. 1(*c*)) to the viscera, almost no adhesions occurred. Only one implantation site showed minor grade 1 adhesion (12.5% incidence), the remaining test sites were free of adhesion. When the implant was wrongly positioned, with the mesh side facing to the viscera, in 87.5% of the cases adhesion occurred, and in more severe grades from 1 to 4.

Thus, the surgical implant according to the invention exhibited a good adhesion reduction when correctly placed with the rough barrier layer side facing the viscera.

TABLE 1

In-vivo performance of samples of the surgical implant according to Example 5 in rabbits

| Treatment groups (n = 8) | Adhesion incidence | Adhesion extent for Grades 0 to 4 |
|---|---|---|
| Sham control | 8/8 (100%) | 1: (2/8), 2: (4/8), 3: (1/8), 4: (1/8) |
| Barrier layer to viscera | 1/8 (12.5%) | 0: (7/8), 1: (1/8) |
| Mesh side to viscera | 7/8 (87.5%) | 0: (1/8), 1: (3/8), 2: (2/8), 4: (2/8) |

The invention claimed is:
1. A surgical implant, comprising
a flexible, areal basic structure comprised of a flat, biocompatible mesh having a first face and a second face and being provided with pores extending from the first face to the second face, and
a barrier layer comprising only a single synthetic, resorbable polymer film, the barrier layer having a first face and a second face and being placed, with its second face, at the first face of the basic structure and being attached to the basic structure without overlapping or being folded over the basic structure,
wherein the barrier layer is deformed into at least part of the pores where it forms, in a respective pore, a barrier region such that the second face of the barrier layer is closer to the second face of the basic structure than the first face of the barrier layer is to the first face of the basic structure, and such that the second face of the barrier layer is exposed through the second face of the basic structure;
wherein the surgical implant is adapted for implantation within a patient's body and configured such that when placed against a tissue surface the second face of the areal basic structure and second face of the barrier layer both directly contact the same tissue surface to be repaired, and wherein when so implanted the barrier layer has an anti-adhesive effect that prevents bodily tissue from growing into the first face of the areal basic structure, and wherein the second face of the barrier layer that is exposed through the pores of the areal basic structure is adapted to cling to the tissue to be repaired but not prevent tissue ingrowth into the areal basic structure through the second face of the areal basic structure.

2. A surgical implant according to claim 1, characterized in that the average roughness, as defined in ASME B46.1-2009 and measured over that area of the basic structure where the barrier layer is deformed into pores of the basic structure, is smaller at the second faces of the barrier layer and the basic structure than at the first faces of the barrier layer and the basic structure.

3. A surgical implant according to claim 2, characterized in that the ratio of the average roughness measured at the second faces of the barrier layer and the basic structure to the average roughness measured at the first faces of the barrier layer and the basic structure has a value in one of the following ranges: 0.0-0.1, 0.1-0.2, 0.2-0.3, 0.3-0.4, 0.4-0.5, 0.5-0.6, 0.6-0.7, 0.7-0.8, 0.8-0.9, 0.9-1.0.

4. A surgical implant according claim 1, characterized in that said barrier region is basically flat.

5. A surgical implant according to claim 4, characterized in that the angle between said barrier region and a plane in parallel to the second face of the basic structure is in the range of from 0° to 5°.

6. A surgical implant according to claim 4, characterized in that said barrier region has a size in the range of from 0.5 mm to 5 mm and less than the size of the respective pore of the basic structure.

7. A surgical implant according to claim 1, characterized by a bonding material having a melting temperature lower than the melting temperature of at least part of the material of the basic structure and lower than the melting temperature of at least part of the material of the barrier layer, wherein the bonding material comprises poly-p-dioxanone.

8. A surgical implant according to claim 1, characterized in that the basic structure is designed in one of the following forms: a surgical mesh, a mesh-like sheet, a spacer fabric, a perforated film, a perforated woven, a perforated nonwoven, a mesh pouch.

9. A surgical implant according to claim 1, characterized in that the pores of the basic structure have a size in the range of from 1 mm to 9 mm.

10. A surgical implant according to claim 1, characterized in that the barrier layer is provided with pores having a smaller size than that of the pores of the basic structure.

11. A surgical implant according to claim 1, characterized in that the barrier layer, between pores of the basic structure, forms ridges where the first face of the barrier layer rises above the first face of the barrier layer in an adjacent barrier region by an amount in the range of from 50 µm to 900 µm.

12. A surgical implant according to claim 1, characterized in that the barrier layer comprises one of the following features: being continuous, being made of a plurality of spaced film pieces.

13. A surgical implant according to claim 1, characterized in that the basic structure comprises a non-absorbable material, at least one of the materials selected from the following list: polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyimides, polyurethanes, polyisoprenes, polystyrenes, polysilicones, polycarbonates, polyarylether ketones, polymethacrylic acid esters, polyacrylic acid esters, aliphatic polyesters, aromatic polyesters, copolymers of polymerizable substances thereof.

14. A surgical implant according to claim 1, characterized in that the basic structure comprises an absorbable material, at least one of the materials selected from the following list: synthetic bioabsorbable polymer materials, polyhydroxy acids, polylactides, polyglycolides, copolymers of glycolide and lactide, copolymers of glycolide and lactide in the ratio 90:10, copolymers of glycolide and lactide in the ratio 5:95, copolymers of lactide and trimethylene carbonate, copolymers of glycolide, lactide and trimethylene carbonate, polyhydroxybutyrates, polyhydroxyvaleriates, polycaprolactones, copolymers of glycolide and ε-caprolactone, polydioxanones, poly-p-dioxanone, synthetic and natural oligo- and polyamino acids, polyphosphazenes, polyanhydrides, polyorthoesters, polyphosphates, polyphosphonates, polyalcohols, polysaccharides, polyethers, collagen, gelatin, bioabsorbable gel films cross-linked with omega 3 fatty acids, oxygenized regenerated cellulose.

15. A surgical implant according to claim 1, characterized in that the barrier layer is designed as a polymeric film and comprises an absorbable material, at least one of the materials selected from the following list: copolymers of glycolide and ε-caprolactone, collagens, gelatine, hyaluronic acid, polyvinyl pyrrolidone, polyvinyl alcohol, fatty acids, polyhydroxy acids, polyether esters, polydioxanones, copolymers of polymerizable substances thereof.

16. A surgical implant according to claim 1, characterized by an orientation marker adapted for distinguishing the first face of the basic structure from the second face of the basic structure.

17. A surgical implant according to claim 1, characterized in that the surgical implant is arranged to be placed with the second face of the basic structure and the second face of the barrier layer towards a patient's peritoneum.

* * * * *